(12) United States Patent
Tao

(10) Patent No.: US 9,024,064 B2
(45) Date of Patent: May 5, 2015

(54) ALANYL GLUTAMINE COMPOUND AND PREPARATION METHOD THEREOF

(75) Inventor: Linggang Tao, Wuyi (CN)

(73) Assignee: Hainan Lingkang Pharmaceutical Co., Ltd., Haikou (CN)

( * ) Notice: Subject to any disclaimer, the term of this patent is extended or adjusted under 35 U.S.C. 154(b) by 0 days.

(21) Appl. No.: 14/119,362

(22) PCT Filed: Dec. 27, 2011

(86) PCT No.: PCT/CN2011/002200
§ 371 (c)(1),
(2), (4) Date: Nov. 22, 2013

(87) PCT Pub. No.: WO2013/078577
PCT Pub. Date: Jun. 6, 2013

(65) Prior Publication Data
US 2015/0038740 A1 Feb. 5, 2015

(30) Foreign Application Priority Data
Nov. 28, 2011 (CN) .......................... 2011 1 0384393

(51) Int. Cl.
| | | |
|---|---|---|
| C07C 231/00 | (2006.01) |
| C07C 237/06 | (2006.01) |
| C07K 1/30 | (2006.01) |
| C07K 5/02 | (2006.01) |
| C07C 231/12 | (2006.01) |
| C07C 231/24 | (2006.01) |
| C07C 237/22 | (2006.01) |
| C07K 5/062 | (2006.01) |

(52) U.S. Cl.
CPC .............. *C07C 231/00* (2013.01); *C07K 1/306* (2013.01); *C07K 5/06026* (2013.01); *C07C 237/06* (2013.01); *C07K 5/0202* (2013.01); *C07C 231/12* (2013.01); *C07C 231/24* (2013.01); *C07C 237/22* (2013.01)

(58) Field of Classification Search
CPC .. C07C 231/00; C07C 237/06; C07C 237/22; C07C 237/24
See application file for complete search history.

(56) References Cited

FOREIGN PATENT DOCUMENTS

| | | |
|---|---|---|
| CN | 101463075 A | 6/2009 |
| EP | 0595345 B1 * | 5/1994 |

OTHER PUBLICATIONS

Baranov et al. Russian Journal of Applied Chemistry (2005), 78(3), p. 470-473.*
Recrystallization at University of Toronto, Chem 249 class, p. 1-18 (downloaded date 2014).*

* cited by examiner

*Primary Examiner* — Yong Chu
(74) *Attorney, Agent, or Firm* — CBM Patent Consulting, LLC

(57) ABSTRACT

A process for preparing a pure alanylglutamine comprises the steps of: 1) reacting N-(α-chloro)-propionyl-glutamine and hydrazine compound to obtain an alanylglutamine crude product; 2) mixing anhydrous methanol and the alanylglutamine crude product to provide a filter cake; 3) dissolving the filter cake in water, heating, adding ethanol, and cooling to yield the pure alanylglutamine.

7 Claims, No Drawings

ALANYL GLUTAMINE COMPOUND AND PREPARATION METHOD THEREOF

This application is the U.S. national phase of International Application No. PCT/CN2011/002200 Filed 27 Dec. 2011 which designated the U.S. and claims priority to Chinese Application No. 201110384393.7 filed 28 Nov. 2011, the entire contents of each of which are hereby incorporated by reference.

FIELD OF THE INVENTION

The present invention relates to a highly pure alanylglutamine compound and its preparation method, and belongs to the medical technical filed.

BACKGROUND ART

Alanylglutamine, with alias N-(2)-L-alanyl-L-glutamine, has the English name L-alanyl-L-glutamine, and the chemical name N-(2)-L-alanyl-L-glutamine. Its molecular formula is $C_9H_{15}N_3O_4$ with a molecular weight of 217.22. The structure of alanylglutamine is as follows:

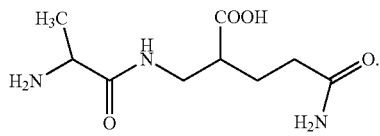

Alanylglutamine was first developed and manufactured by Germany's Fresenius AG, and imported into China in 1999. As a parenteral nutrition drug, alanylglutamine can be used to improve patients' cellular immune function, to effectively reduce the risk of infection in critically ill patients, to play an important role especially in the treatment and recovery of severe infections, malignant cancers and other serious injuries, and to shorten the total time length of patient hospitalization. Clinical studies have shown that Gln has good therapeutic effects towards severe metabolic disorders (such as burns/trauma/major surgery, acute and chronic infections, bone marrow transplantation, and multiple organ dysfunction syndrome), bowel dysfunction (such as short bowel syndrome, colitis and chemotherapy induced mucosal damage), and immune deficiency syndrome (such as AIDS, critical illness or bone marrow transplantation associated immune dysfunction). Alanylglutamine can effectively maintain the total number of lymphocytes in the blood circulation, and relieve surgery and chemotherapy-induced immunosuppression, which may be related to the adequate breathing fuel provided to lymphocytes by the Ala-Gln. Alanylglutamine is an very effective parenteral nutrition drug. It can reduce body proteolysis of the gastrointestinal cancer patients after surgery and chemotherapy, effectively improve the nitrogen balance and maintain the number of lymphocytes in the blood circulation, therefore improve patients' nutritional conditions and enhance body tolerance to surgery and chemotherapy.

A number of domestic and foreign references of patents and journals have disclosed processes for synthesizing alanylglutamine. For example:

European Patent EPNO311.057 uses benzyloxycarbonylalanine (Z-ALa) to generate an activated ester in the presence of dicyclohexyl carbodiimide (DCC), condensation with glutamine (Gln) to synthesize a dipeptide, and then deprotection by catalytic hydrogenation to provide alanylglutamine. This method has relatively lengthy steps and requires hydrogenation to remove the protecting group.

In European Patent 595345 (EP595345), water immiscible organic solvents (generally toluene, chloroform and methylene chloride) are used in the reaction between optically pure α-halopropionyl halides and glutamine under low temperature and pH 10 conditions to provide optically pure α-halopropionyl glutamine, which is aminated in aqueous ammonia to provide alanylglutamine. The disadvantage of this method is that optically pure halopropionyl halides are hard to acquire and expensive. Additionally, in the above method, only one of the two diastereomeric isomers: L-alanyl-L-glutamine and D-alanyl-L-glutamine can be obtained in each preparation, which limits the promotion of its applications.

Chinese Patent CN1392156 discloses a process for preparing alanylglutamine, wherein N-protected amino acid reacts with triphenylphosphine, hexachloroethane in an organic solvent to form an active ester; the active ester reacts with glutamine in a mixed aqueous solution of an inorganic base and an organic solvent, then acidification is carried out with an inorganic acid followed by removal of the N-terminal protecting group to provide alanylglutamine. But the reaction generates main product alanylglutamine dipeptide along with byproduct triphenylphosphine oxide.

Chinese Patent CN1786019A discloses a process for preparing alanylglutamine, including the steps wherein esterified L-lactic acid reacts with thionyl chloride in the presence of a catalyst to give 2-chloropropionate; 2-chloropropionate is hydrolyzed with basic solution to give 2-chloropropionic acid; 2-chloropropionic acid reacts with a chlorinating reagent to give 2-chloropropionic chloride; 2-chloropropionic chloride reacts with L-glutamine to provide N-(2-chloro)-propionyl-glutamine; N-(2-chloro)-propionyl-glutamine reacts with aqueous ammonia to generate alanylglutamine dipeptide product. However, in the industrial production processes applying this synthetic method, due to the presence of impurities such as ammonium chloride in the reaction solution, crystallization is needed to remove salts. Currently conventional methods for desalination in the alanylglutamine production processes involve desalting by crystallization using alcohols (e.g. methanol, ethanol, isopropanol etc.) and water.

Therefore, a simple method for preparation and purification of alanyl-L-glutamine is still needed to provide alanylglutamine compound with high purity.

DETAILED DESCRIPTION OF THE INVENTION

The purpose of the present invention is to provide a highly pure alanylglutamine compound, for which a method for preparation and purification of alanyl-L-glutamine is presented. Alanylglutamine crude product is generated using N-(α-chloro)-propionyl-glutamine as starting material and selected hydrazine compound as amination reagent. After necessary workup procedures for purification, extremely pure target compound can be obtained, hence improving the quality of formulated products, reducing side effects and ensuring safety in clinical applications.

After studies, the inventors found that highly pure alanylglutamine compound can be obtained by a preparation process which comprises the steps of:
1) using N-(α-chloro)-propionyl-glutamine as starting material and selected hydrazine compounds as amination reagents, conducting the reaction at atmospheric pressure to obtain alanylglutamine crude product;
2) adding anhydrous methanol to the alanylglutamine crude product under 0° C. to room temperature with stifling, followed by filtering to remove methanol solution, to provide a filter cake containing alanylglutamine;

3) dissolving the filter cake containing alanylglutamine in water, heating the resulting aqueous solution to no higher than 80° C. and keeping at that temperature for a certain time to concentrate, followed by adding ethanol, with the volume ratio of aqueous solution to ethanol being 1:1~3, and gradient cooling to provide the purified alanylglutamine via recrystallization.

The following is detailed description of the invention.

In step 1) of the present invention, using N-(α-chloro)-propionyl-glutamine as starting material and selected hydrazine compounds as amination reagents, the reaction is conducted at atmospheric pressure to provide alanylglutamine crude product.

N-(α-chloro)-propionyl-glutamine is a known chemical, and can be purchased, or prepared according to known method, for example:

It may be prepared according to Chinese Patent CN1786019A, wherein, esterified L-lactic acid reacts with thionyl chloride in the presence of a catalyst to give 2-chloropropionate; 2-chloropropionate is hydrolyzed with basic solution to give 2-chloropropionic acid; 2-chloropropionic acid reacts with a chlorinating reagent to give 2-chloropropionic chloride; 2-chloropropionic chloride reacts with L-glutamine to provide N-(2-chloro)-propionyl-glutamine.

It may also be prepared according to Chinese Patent CN1680428A, wherein, under room temperature L-glutamine, with 0.5-1.0 molar ratio to α-haloacyl halide, is added into a mixture of toluene and water with 10 times volume, which has a toluene to water ratio of 1:2. After cooling to 2° C.~5° C., 5N sodium hydroxide, with 1:1 molar ratio to glutamine, is added into the system to dissolve L-glutamine. Under the temperature of 2° C.~5° C., a solution consisting of α-halopropionyl halide with 2:1-1:1 molar ratio to L-glutamine, toluene two times the volume of α-halopropionyl halide, and 5N sodium hydroxide 1.5 times the volume of α-halopropionyl halide, is added slowly to the reaction system over a period of 1-4 hours. 5N sodium hydroxide is used to adjust the pH value to 9~11, and the reaction is kept under 5° C.~20° C. temperature for 1-6 hours, after which organic layer is separated. Under room temperature, solid sodium chloride with 3:1 molar ratio to L-glutamine is added into the mixture solution with separated organic layer, and with stifling, concentrated hydrochloric acid is added drop wise to adjust the pH value to 2~3.5, after which more concentrated hydrochloric acid is added to adjust the pH value to 0.5~1.5. After settling at room temperature for 2~8 hours, N-(α-halopropionyl)-L-glutamine crystallizes out and can be retrieved by filtration.

According to the technical solution in the present invention, in step 1), N-(α-halopropionyl)-L-glutamine is aminated with hydrazine compounds, preferably hydrazine, methyl hydrazine or ethyl hydrazine, or hydrazine hydrate.

In the prior art ammonia is used as amination reagent. For example, in CN1680428A, N-α-halopropionyl)-L-glutamine crystals, after being dried, is mixed with 28% aqueous ammonia with 1:10~1:30 weight ratio in a reaction vessel, and the reaction is carried out under 10° C.~60° C. temperature and 2 kg/cm² pressure for 4~12 hours, then cooled to room temperature, concentrated under reduced pressure, and charged with water with a solution to water volume ratio of 2:1.

The inventors found that if hydrazine compounds are used as amination reagents, the amination reaction can be done under atmospheric pressure, due to the fact that hydrazine compounds are generally liquid and miscible with water, which is beneficial to amination. The hydrazine compounds may be hydrazine, methyl hydrazine or ethyl hydrazine, or hydrazine hydrate. The concentration of the hydrazine hydrate may be 35%, 40%, 55%, 64%, 80%, 85% or 100%.

Additionally, hydrazine compounds can be stoichiometric or slightly excess amount in the reaction, such as 5~50% excess stoichiometry, rather than significantly excess as in the case of ammonia, therefore avoiding many byproducts generated by excess amount of ammonia. The reason might be that comparing with ammonia, amino group or alkylamino group in hydrazine compounds, replacing proton in ammonia, makes hydrazine more reactive, and hence easier to react with N-(α-chloro)-propionyl-glutamine and replace the chlorine at a position with amino group.

According to the present invention, N-(α-chloro)-propionyl-glutamine is dissolved in water, and with the use of hydrazine as amination reagent, the reaction is carried out under atmospheric pressure, at 30~70° C. temperature, for 5~20 hours, then concentrated and cooled under low temperature to provide alanylglutamine crude product as precipitates.

In step 2) of the present invention, anhydrous methanol is added to the alanylglutamine crude product under 0° C. to room temperature with stifling, followed by filtering to remove methanol solution, to provide a filter cake containing alanylglutamine.

In prior art, such as CN1164611C, CN1302008C, CN1315868C, CN1680428A and CN10162938B, methods for preparation of alanylglutamine are disclosed. However, alanyl-L-glutamine prepared using these methods contains many related impurities and single impurity is greater than 0.5%, which is not suitable for formulation of pharmaceutical injections. Related impurities mainly are alanine, glutamine, pyroglutamic acid, alanyl-L-glutamine rings, and triphenylphosphine oxide.

In step 1) of the present invention, when alanylglutamine crude product is obtained, the number and quantities of the above mentioned impurities in the crude product are significantly lowered, but byproducts still exist in trace amounts.

The inventors found that some of these byproducts in trace amounts are soluble in methanol, whereas target product alanylglutamine barely dissolves in methanol.

Therefore, under relatively low temperature, preferably 0° C. to room temperature, anhydrous methanol is added to the alanylglutamine crude product, with the volume of anhydrous methanol being half of the volume of the alanylglutamine, or at most equivalent to the volume of the alanylglutamine, i.e. the methanol liquid surface covers all alanylglutamine. Then vigorous stirring is conducted to form a slurry or suspension, followed by filtration to remove methanol solution, to provide a filter cake containing alanylglutamine. The filter cake is washed with methanol for several times, preferably 2-5 times, with the volume of methanol for washing being one third to one half of the volume of the slurry or suspension.

According to the present invention, the methanol solution obtained after filtration or washing may be recycled in this step, so the small amount of target product that is dissolved in the methanol solution can be further processed, effectively avoiding loss of alanylglutamine.

In step 3) of the present invention, the filter cake containing alanylglutamine is dissolved in water, and the resulting aqueous solution is heated to no higher than 80° C. The solution is kept at that temperature for a certain period of time to concentrate, followed by adding ethanol, preferably ethanol with higher than 80% purity, more preferably ethanol with 95% purity, most preferably anhydrous ethanol, with a volume ratio of the aqueous solution to the ethanol being 1:1~3, more preferably with a volume ratio of 1:1~2, most preferably with a volume ratio of 1:1~1.5. Then gradient cooling is done to provide the purified alanylglutamine via recrystallization.

The inventors found through studies that alanylglutamine aqueous solution recrystallizes well when a mixed solvent of water and ethanol with specified volume ratio is used. Compared with the use of water alone, the use of water and ethanol mixed solvent makes recrystallization process better. On one hand, crystallization goes smoothly, more easily crystallized than pure water as a solvent, due to the lower solubility of alanylglutamine in ethanol than in water, and the presence of ethanol making crystallization easier. On the other hand, the resulting crystals have high purity, and contain almost no other impurities. Furthermore, effective combination of a mixed solvent with subsequent gradient cooling gives unexpected effects on the recrystallization rate and the crystal purity, by controlling the concentration of the mixed solvent and recrystallization temperature.

Surprisingly, after the processes of the steps 1) and 2) of the present invention, crystals with high purity are obtained when the mixed solvent is used in crystallization of alanylglutamine. The reason may be that the impurities that adversely affect crystallization are removed by the steps 1) and 2) of the present invention.

The inventors found through studies that recrystallization proceeds well under gradient cooling conditions.

In a preferred embodiment of the present invention, the filter cake containing alanylglutamine is dissolved in water, and the resulting aqueous solution is heated to no higher than 80° C., preferably no higher than 70° C., more preferably no higher than 65° C. After the solution is kept at that temperature for a certain period of time to concentrate, followed by adding ethanol, the gradient cooling process includes three cooling intervals:

In the first cooling interval, temperature drops from the system temperature after concentrating and addition of ethanol to 55° C. with a rate of 1-3° C./hour. In the second cooling interval, temperature drops from 55° C. to 20° C. with a rate of 3-5° C./hour. In the third cooling interval, temperature drops from 20° C. to 0-4° C. with a rate of 5-6° C./hour.

More preferably, in the first cooling interval, temperature drops with a rate of 1.5-2.5° C./hour, preferably about 2° C./hour. More preferably, in the second cooling interval, temperature drops with a rate of about 4° C./hour. More preferably, in the third cooling interval, temperature drops with a rate of about 5° C./hour.

Without being bound by theory, the inventors believe that the reasons that gradient cooling is good for recrystallized may be as follows: in high temperature range, by controlling the slow decrease of temperature, uneven precipitation of crystals is avoided, and crystal growing points of uniform size and even distribution are formed; in moderate to low temperature range, the proper increase of rate of temperature dropping helps the rapid growth of the already formed crystals.

After crystallization is completed, centrifugation is conducted, followed by washing and drying. Washing may be done with methanol. Drying may be done by air drying or vacuum drying method.

The refined alanylglutamine obtained from the above embodiments shows that the content of alanylglutamine is no less than 99.7%, even as high as 99.9%, according to the high-performance liquid chromatography measurement, and the color is white.

Since the powder flowability, specific dissolution rate, solid stability of alanylglutamine and the operability of the process play important roles in the activity of alanylglutamine and the formulations prepared thereof, alanylglutamine with substantially increased purity brings about significant improvements in the dissolution rate, the formulatability and the stability.

Therefore, the alanylglutamine refined according to the process of the present invention is highly suitable to be formulated into a parenteral nutrition drug, which can be used to improve patients' cellular immune function, to effectively reduce the risk of infection in critically ill patients, to play an important role especially in the treatment and recovery of severe infections, malignant cancers and other serious injuries, to shorten the total time length of patient hospitalization, and to have good therapeutic effects towards severe metabolic disorders (such as burns/trauma/major surgery, acute and chronic infections, bone marrow transplantation, and multiple organ dysfunction syndrome), bowel dysfunction (such as short bowel syndrome, colitis and chemotherapy induced mucosal damage), and immune deficiency syndrome (such as AIDS, critical illness or bone marrow transplantation associated immune dysfunction). For example, alanylglutamine can reduce body proteolysis of the gastrointestinal cancer patients after surgery and chemotherapy, effectively improve the nitrogen balance and maintain the number of lymphocytes in the blood circulation, therefore improve patients' nutritional conditions and enhance body tolerance to surgery and chemotherapy.

Thus alanylglutamine is suitable for the preparation of a pharmaceutical composition for parenteral nutrition, which comprises refined alanylglutamine according to the present invention and pharmaceutically acceptable excipients. Preferably, the pharmaceutical compositions may be injections or granular formulations The present invention has fundamentally changed the current situation of low purity of the alanylglutamine material, solved the problems existing in alanylglutamine crude material and alanylglutamine drug substances, and reduced a series of clinical adverse reactions due to the presence of excessive impurities. The present invention also has advantages of convenience, ease for control and industrialization.

Embodiments of the Invention

The following examples are intended to further explain or illustrate the present invention, and the examples provided should not be understood as limiting the protective scope of the present invention.

The Purity Measurement of Alanylglutamine by HPLC:

Purity is determined by the high performance liquid chromatography method (Chinese Pharmacopoeia 2010 Edition part two Appendix VD).

Chromatographic conditions and system suitability test: amino-bonded silica gel as fillers, 0.05 mol/L potassium dihydrogen phosphate buffer solution (pH adjusted to 4.0 with phosphoric acid)-acetonitrile (30:70) as the mobile phase, with detection wavelength at 215 nm and flow rate of 0.8 ml/min. Degree of separation between L-pyroglutamyl-L-alanine and L-pyroglutamic acid should be no less than 1.0.

Detailed procedures: 20 μL of the control solution is injected into the liquid chromatograph and the detection sensitivity is adjusted to make the height of cyclic-(L-alanyl-L-glutamine) chromatographic peak not less than 10% of the full scale of recorder. Inject 20 μL of the test solution into the liquid chromatograph, record the chromatograms to 3 times of the main component peak retention time. Contents of the known impurities are calculated by external standard method.

Example 1

Refinement of Alanylglutamine 0.2 Mol of purchased N-(α-chloro)-propionyl-glutamine is dissolved in 1000 mL water, and 0.25 mol of hydrazine is added into the solution. The reaction is conducted at atmospheric pressure, under the temperature of 50~55° C., for 10~15 hours, followed by concentrating and cooling under 10° C. to precipitate out alanylglutamine crude product, which has alanylglutamine content of 92.80% as determined by HPLC.

Under 15° C. temperature, anhydrous methanol is added to the alanylglutamine crude product, with the volume of anhydrous methanol being half of the volume of the alanylglutamine. Then vigorous stirring is conducted to form a slurry, followed by filtration to remove methanol solution, to provide a filter cake containing alanylglutamine. The filter cake is washed with methanol for three times, with the volume of methanol for every washing being one third of the volume of the slurry or suspension. In this step, the methanol solutions obtained after filtration and washing are recycled, so that the small amount of alanylglutamine that is dissolved in the methanol solutions can be further processed. But the recycle process repeats at most five times, after which the methanol solutions obtained after filtration and washing are discarded.

The filter cake containing alanylglutamine is dissolved in water, and the resulting aqueous solution is heated to 70-75° C. The solution is kept at that temperature for half hour, followed by adding anhydrous ethanol, with a volume ratio of the aqueous solution to the ethanol being 1:2. First the temperature drops to 55° C. with a rate of 2° C./hour. Then the temperature drops to 20° C. with a rate of 4° C./hour. Last, the temperature drops to 5° C. with a rate of 5° C./hour. Crystals form over the cooling processes. After being settled for 5 hours, the crystals are filtered out and washed with methanol, followed by drying under 50° C. to yield 38.4 g refined alanylglutamine.

The melting point is 215.5~216° C. and the purity is measured as 99.83% by High Performance Liquid Chromatography (HPLC).

MS (m/z): 218 ($M^{+1}$); UVMAX (water): 191.5 nm.

IR ($cm^{-1}$): 3407, 3331, 3226, 2981, 2933, 1642; 1534, 1385, 1113;

$^1$H-NMR: 4.166, 4.117, 2.325, 2.134, 1.977, 1.537 ppm;

$^{13}$C-NMR: 178.146, 177.352, 169.847, 54.624, 48.721, 31.322, 27.174, 16.093 ppm.

Comparative Example 1

Refinement of Alanylglutamine (Methanol not Used to Remove Impurities)

0.2 Mol of purchased N-(α-chloro)-propionyl-glutamine is dissolved in 1000 mL water, and 0.25 mol of hydrazine is added into the solution. The reaction is conducted at atmospheric pressure, under the temperature of 50~55° C., for 10~15 hours, followed by concentrating and cooling under 10° C. to precipitate out alanylglutamine crude product, which has alanylglutamine content of 92.80% as determined by HPLC.

The alanylglutamine crude product is dissolved in water, and the resulting aqueous solution is heated to 70-75° C. The solution is kept at that temperature for half hour, followed by adding anhydrous ethanol, with a volume ratio of the aqueous solution to the ethanol being 1:2. First the temperature drops to 55° C. with a rate of 2° C./hour. Then the temperature drops to 20° C. with a rate of 4° C./hour. Last, the temperature drops to 5° C. with a rate of 5° C./hour. Crystals form over the cooling processes. After being settled for 5 hours, the crystals are filtered out and washed with methanol, followed by drying under 50° C. to yield 35.4 g refined alanylglutamine.

The melting point is 213~218° C. and the purity is measured as 96.83% by High Performance Liquid Chromatography (HPLC). The reason is that alanylglutamine crude product wraps small amount of impurities, which can precipitate out together with the target product during crystallization process.

Example 2

Refinement of Alanylglutamine 0.2 Mol of purchased N-(α-chloro)-propionyl-glutamine is dissolved in 1300 mL water, and 0.22 mol of hydrazine is added into the solution. The reaction is conducted at atmospheric pressure, under the temperature of 45~50° C., for 12~15 hours, followed by concentrating and cooling under 15° C. to precipitate out alanylglutamine crude product, which has alanylglutamine content of 93.20% as determined by HPLC.

Under 14° C. temperature, anhydrous methanol is added to the alanylglutamine crude product, with the volume of anhydrous methanol being half of the volume of the alanylglutamine. Then vigorous stirring is conducted to form a slurry, followed by filtration to remove methanol solution, to provide a filter cake containing alanylglutamine. The filter cake is washed with methanol for four times, with the volume of methanol for every washing being half the volume of the slurry or suspension. In this step, the methanol solutions obtained after filtration and washing are recycled, so that the small amount of alanylglutamine that is dissolved in the methanol solutions can be further processed. After the recycle process repeats four times, the methanol solutions obtained after filtration and washing are discarded.

The filter cake containing alanylglutamine is dissolved in water, and the resulting aqueous solution is heated to 72-78° C. The solution is kept at that temperature for one hour, followed by adding 95% ethanol, with a volume ratio of the aqueous solution to the ethanol being 1:2.5. First the temperature drops to 55° C. with a rate of 2.5° C./hour. Then the temperature drops to 20° C. with a rate of 3° C./hour. Last, the temperature drops to 5° C. with a rate of 5° C./hour. Crystals form over the cooling processes. After being settled for 6 hours, the crystals are filtered out and washed with methanol, followed by drying under 50° C. to yield 37.8 g refined alanylglutamine.

The melting point is 215.4~215.8° C. and the purity is measured as 99.88% by High Performance Liquid Chromatography (HPLC).

MS (m/z): 218 ($M^{+1}$); UVMAX (water): 191.5 nm.

$^1$H-NMR: 4.168, 4.119, 2.324, 2.133, 1.975, 1.538 ppm;

$^{13}$C-NMR: 178.148, 177.354, 169.848, 54.625, 48.722, 31.324, 27.175, 16.091 ppm.

Comparative Example 2

Refinement of Alanylglutamine (Gradient Cooling not Conducted)

0.2 Mol of purchased N-(α-chloro)-propionyl-glutamine is dissolved in 1000 mL water, and 0.25 mol of hydrazine is added into the solution. The reaction is conducted at atmospheric pressure, under the temperature of 45~50° C., for 12~15 hours, followed by concentrating and cooling under 15° C. to precipitate out alanylglutamine crude product, which has alanylglutamine content of 93.20% as determined by HPLC.

Under 15° C. temperature, anhydrous methanol is added to the alanylglutamine crude product, with the volume of anhydrous methanol being half of the volume of the alanylglutamine. Then vigorous stirring is conducted to form a slurry, followed by filtration to remove methanol solution, to provide a filter cake containing alanylglutamine. The filter cake is washed with methanol for three times, with the volume of methanol for every washing being ⅓ the volume of the slurry or suspension. In this step, the methanol solutions obtained after filtration and washing are recycled, so that the small amount of alanylglutamine that is dissolved in the methanol solutions can be further processed. After the recycle process repeats three times, the methanol solutions obtained after filtration and washing are discarded.

The filter cake containing alanylglutamine is dissolved in water, and the resulting aqueous solution is heated to 70-75° C. The solution is kept at that temperature for half hour, followed by adding anhydrous ethanol, with a volume ratio of the aqueous solution to the ethanol being 1:2. The temperature drops to 5° C. after 5 hours. Crystals form over the cooling processes. After being settled for 5 hours, the crystals are filtered out and washed with methanol, followed by drying under 50° C. to yield 33.4 g refined alanylglutamine.

The melting point is 212~217° C. and the purity is measured as 95.53% by High Performance Liquid Chromatography (HPLC). The reason is that crystallization process is so fast that initial growth of crystal nuclei is uneven, and rapid crystallization causes some incomplete crystallization or polycrystalline materials to precipitate with the desired product.

Example 3

Refinement of Alanylglutamine 0.2 Mol of N-(α-chloro)-propionyl-glutamine prepared according to CN1786019A, melting point 147~152° C., is dissolved in 1200 mL water, and 0.3 mol of methyl hydrazine is added into the solution. The reaction is conducted at atmospheric pressure, under the temperature of 40~45° C., for 16~18 hours, followed by concentrating and cooling under 12° C. to precipitate out alanylglutamine crude product, which has alanylglutamine content of 85.6% as determined by HPLC.

Under 12° C. temperature, anhydrous methanol is added to the alanylglutamine crude product, with the volume of anhydrous methanol being equal to the volume of the alanylglutamine. Then vigorous stirring is conducted to form a suspension, followed by filtration to remove methanol solution, to provide a filter cake containing alanylglutamine. The filter cake is washed with methanol for five times, with the volume of methanol for every washing being half the volume of the slurry or suspension. In this step, the methanol solutions obtained after filtration and washing are recycled, so that the small amount of alanylglutamine that is dissolved in the methanol solutions can be further processed. In order to avoid interference of the impurities therein, after the recycle process repeats twice, the methanol solutions obtained after filtration and washing are discarded.

The filter cake containing alanylglutamine is dissolved in water, and the resulting aqueous solution is heated to 68-72° C. The solution is kept at that temperature for half hour, followed by adding 95% ethanol, with a volume ratio of the aqueous solution to the ethanol being 1:1.8. First the temperature drops to 55° C. with a rate of 1.8° C./hour. Then the temperature drops to 20° C. with a rate of 3° C./hour. Last, the temperature drops to 5° C. with a rate of 5.5° C./hour. Crystals form over the cooling processes. After being settled for 6 hours, the crystals are filtered out and washed with methanol, followed by drying under 45° C. to yield 34.4 g refined alanylglutamine.

The melting point is 215.6~216.0° C. and the purity is measured as 99.78% by High Performance Liquid Chromatography (HPLC).

MS (m/z): 218 ($M^{+1}$); UVMAX (water): 191.5 nm.
$^1$H-NMR: 4.167, 4.115, 2.326, 2.132, 1.979, 1.535 ppm;
$^{13}$C-NMR: 178.145, 177.354, 169.845, 54.626, 48.723, 31.320, 27.173, 16.094 ppm.

Comparative Example 3

Refinement of Alanylglutamine (Ammonia Used as Amination Reagent)

Alanylglutamine is prepared according to CN1786019A. Wherein, esterified L-lactic acid reacts with thionyl chloride in the presence of a catalyst to give 2-chloropropionate; 2-chloropropionate is hydrolyzed with basic solution to give 2-chloropropionic acid; 2-chloropropionic acid reacts with a chlorinating reagent to give 2-chloropropionic chloride; 2-chloropropionic chloride reacts with L-glutamine to provide N-(2-chloro)-propionyl-glutamine; N-(2-chloro)-propionyl-glutamine reacts with aqueous ammonia to generate alanylglutamine crude product. However, the reaction solution contains salt impurities such as ammonium chloride, which causes difficulties in subsequent purification processes.

Example 4

Refinement of Alanylglutamine 0.2 Mol of N-(α-chloro)-propionyl-glutamine prepared according to CN1786019A, melting point 147~152° C., is dissolved in 1500 mL water, and 0.21 mol of ethyl hydrazine is added into the solution. The reaction is conducted at atmospheric pressure, under the temperature of 55~60° C., for 15~16 hours, followed by concentrating and cooling under 10° C. to precipitate out alanylglutamine crude product, which has alanylglutamine content of 84.9% as determined by HPLC.

Under 18° C. temperature, anhydrous methanol is added to the alanylglutamine crude product, with the volume of anhydrous methanol being ⅔ of the volume of the alanylglutamine. Then vigorous stirring is conducted to form a slurry, followed by filtration to remove methanol solution, to provide a filter cake containing alanylglutamine. The filter cake is washed with methanol for four times, with the volume of methanol for every washing being ⅓ the volume of the slurry or suspension. In this step, the methanol solutions obtained after filtration and washing are recycled. After the recycle process repeats three times, the methanol solutions obtained after filtration and washing are discarded.

The filter cake containing alanylglutamine is dissolved in water, and the resulting aqueous solution is heated to 65-70° C. The solution is kept at that temperature for half hour, followed by adding 85% ethanol, with a volume ratio of aqueous solution to the ethanol being 1:3. First the temperature drops to 55° C. with a rate of 2.5° C./hour. Then the temperature drops to 20° C. with a rate of 5° C./hour. Last, the temperature drops to 5° C. with a rate of 6° C./hour. Crystals form over the cooling processes. After being settled for 8 hours, the crystals are filtered out and washed with methanol, followed by drying under 50° C. to yield 33.4 g refined alanylglutamine.

The melting point is 215.5~215.9° C. and the purity is measured as 99.80% by High Performance Liquid Chromatography (HPLC).

MS (m/z): 218 ($M^{+1}$); UVMAX (water): 191.5 nm.
$^1$H-NMR: 4.164, 4.115, 2.324, 2.136, 1.975, 1.536 ppm;
$^{13}$C-NMR: 178.145, 177.353, 169.846, 54.623, 48.724, 31.320, 27.175, 16.092 ppm.

Example 5

Refinement of Alanylglutamine 0.2 Mol of N-(α-chloro)-propionyl-glutamine prepared according to CN1680428A, melting point 146~152° C., is dissolved in 2000 mL water, and 0.3 mol of methyl hydrazine is added into the solution. The reaction is conducted at atmospheric pressure, under the temperature of 55~65° C., for 8~12 hours, followed by concentrating and cooling under 5° C. to precipitate out alanylglutamine crude product, which has alanylglutamine content of 86.9% as determined by HPLC.

Under 15° C. temperature, anhydrous methanol is added to the alanylglutamine crude product, with the volume of anhydrous methanol being ⅗ of the volume of the alanylglutamine. Then vigorous stirring is conducted to form a slurry, followed by filtration to remove methanol solution, to provide a filter cake containing alanylglutamine. The filter cake is washed with methanol for four times, with the volume of methanol for every washing being ½ the volume of the slurry or suspension. In this step, the methanol solutions obtained after filtration and washing are recycled. After the recycle process repeats three times, the methanol solutions obtained after filtration and washing are discarded.

The filter cake containing alanylglutamine is dissolved in water, and the resulting aqueous solution is heated to 75-80° C. The solution is kept at that temperature for half hour, followed by adding 95% ethanol, with a volume ratio of the aqueous solution to the ethanol being 1:2. First the temperature drops to 55° C. with a rate of 2° C./hour. Then the temperature drops to 20° C. with a rate of 4° C./hour. Last, the temperature drops to 5° C. with a rate of 5° C./hour. Crystals form over the cooling processes. After being settled for 7 hours, the crystals are filtered out and washed with methanol, followed by drying under 50° C. to yield 34.4 g refined alanylglutamine.

The melting point is 215.5~216.0° C. and the purity is measured as 99.82% by High Performance Liquid Chromatography (HPLC).

MS (m/z): 218 ($M^{+1}$); UVMAX (water): 191.5 nm.
$^1$H-NMR: 4.163, 4.115, 2.324, 2.132, 1.975, 1.538 ppm;
$^{13}$C-NMR: 178.145, 177.354, 169.845, 54.623, 48.723, 31.323, 27.172, 16.091 ppm.

Example 6

Refinement of Alanylglutamine 0.2 Mol of N-(α-chloro)-propionyl-glutamine prepared according to CN1680428A, melting point 146~152° C., is dissolved in 1800 mL water, and 0.3 mol of 80% hydrazine hydrate is added into the solution. The reaction is conducted at atmospheric pressure, under the temperature of 50~56° C., for 10~15 hours, followed by concentrating and cooling under 15° C. to precipitate out alanylglutamine crude product, which has alanylglutamine content of 87.9% as determined by HPLC.

Under 12° C. temperature, anhydrous methanol is added to the alanylglutamine crude product, with the volume of anhydrous methanol being 3/7 of the volume of the alanylglutamine. Then vigorous stirring is conducted to form a slurry, followed by filtration to remove methanol solution, to provide a filter cake containing alanylglutamine. The filter cake is washed with methanol for four times, with the volume of methanol for every washing being ⅓ the volume of the slurry or suspension. In this step, the methanol solutions obtained after filtration and washing are recycled. After the recycle process repeats three times, the methanol solutions obtained after filtration and washing are discarded.

The filter cake containing alanylglutamine is dissolved in water, and the resulting aqueous solution is heated to 68-70° C. The solution is kept at that temperature for half hour, followed by adding anhydrous ethanol, with a volume ratio of the aqueous solution to the ethanol being 1:2. First the temperature drops to 55° C. with a rate of 2° C./hour. Then the temperature drops to 20° C. with a rate of 3° C./hour. Last, the temperature drops to 5° C. with a rate of 5° C./hour. Crystals form over the cooling processes. After being settled for 6 hours, the crystals are filtered out and washed with methanol, followed by drying under 50° C. to yield 34.8 g refined alanylglutamine.

The melting point is 215.3~215.8° C. and the purity is measured as 99.89% by High Performance Liquid Chromatography (HPLC).

$^1$H-NMR: 4.164, 4.116, 2.324, 2.135, 1.975, 1.538 ppm;
$^{13}$C-NMR: 178.145, 177.351, 169.845, 54.622, 48.724, 31.325, 27.173, 16.094 ppm.

Comparative Example 4

Refinement of Alanylglutamine (Ammonia Used as Amination Reagent)

Alanylglutamine is prepared according to Chinese Patent CN1680428A. Wherein, N-α-chloropropionyl)-L-glutamine is synthesized first. Then, 0.12 g of the N-(α-chloropropionyl)-L-glutamine crystals containing two diastereomeric isomers and 300 mL of 28% aqueous ammonia are mixed in a reaction vessel under room temperature. The reaction is carried out under 60° C. temperature and 2 kg/cm$^2$ pressure. L-Alanyl-L-glutamine crude product is obtained after workup procedures. TLC shows an $R_f$ value of 0.14, with acetate:n-butanol:water (1:4:1) eluent and ninhydrin stain. The above L-alanyl-L-glutamine crude product is dissolved in water, charged with activated carbon, and stirred under room temperature. Then the activated carbon is filtered out, mother crystals are added into the solution, and the system is settled for a while.

Ethanol is added and the system is stirred for 2 hours under room temperature, followed by filtration to provide L-alanyl-L-glutamine solid. Final purification uses Sephadex G-10 column chromatography, with 0.5% acetic acid aqueous solution as eluent and ultraviolet (UV) 210 nm detection. Fractions with Rf value of 0.14 are collected, and concentrated to provide refined product, which has purity of 94.80% as determined by HPLC.

This preparation process is complex, which involves difficult control of the pH value, and formation of salt byproducts. Besides, during amination using ammonia, the reaction pressure differs from atmospheric pressure and prior crystallization and drying of the N-α-chloropropionyl)-L-glutamine are necessary.

The above examples and comparative examples fully illustrate from different aspects the superiority of the present invention and specific combinations thereof, which bring unexpected results that are not reasonably expected theoretically. Without being limited by theory, it may be reasoned that various purification methods have different effects on removing impurities from the drug. The present invention discloses a purification method that has substantial characteristics and significant advances, achieves unexpected technical effects, and provides product with high yields and high purity.

It should be understood that although the present invention has been illustrated according to the above examples, the foregoing description is intended to illustrate, but not to limit in any way the contents of the present invention. Based on the description herein, numerous modifications and embodiments may be devised by the skilled in the art to maximize the use of the present invention, without deviating the spirit and essence of the present invention. Such modifications are also understood to fall within the protective scope of the present invention. Various reference literatures cited in the present disclosure, are hereby fully cited as references.

What is claimed is:

1. A process for separating an alanylglutamine from a crude product,
    said crude product containing one or more non-alanylglutamine compounds selecting from the group consisting of N-(α-chloro)-propionyl-glutamine, hydrazine, methyl hydrazine, ethyl hydrazine and hydrazine hydrate, comprising:
    step 1) mixing anhydrous methanol and the crude product at the temperature between 0° C. and room temperature, then filtering to remove methanol solution, which yields a filter cake containing alanylglutamine;
    step 2) dissolving the filter cake with water, heating the resulting aqueous solution up to 80° C., and keeping at that temperature for a period of time to concentrate, then adding one to three fold of ethanol to the aqueous solution by volume, and cooling gradually to yield a pure alanylglutamine by recrystallization;
    wherein, the cooling process in the step 2) consists of three cooling intervals: in the first cooling interval, the temperature cooling from the system temperature to 55° C. by a rate of 1-3° C./hour after concentrating and addition of ethanol; in the second cooling interval, the temperature cooling from 55° C. to 20° C. by a rate of 3-5° C./hour; in the third cooling interval, the temperature cooling from 20° C. to the temperature between 0 and 4° C. by a rate of 5-6° C./hour.

2. The process according to claim 1, a vigorous stirring is conducted to form a slurry or suspension when 0.5-1 fold of methanol to the crude product by volume is added in the step 2); and the filter cake is washed with methanol for B several times, with the amount of methanol for washing being one third to one half of the slurry or suspension by volume.

3. The process according to claim 1, the methanol solution obtained from filtration in the step 2) is recyclable.

4. The process according to claim 2, the methanol solution obtained from washing in the step 1) is recyclable.

5. The process according to claim 1, the heating temperature for the resulting aqueous solution in step 3) is lower than 70° C.; the concentration of ethanol used in the step 3) is 80 to 100%; the ratio of the aqueous solution to the ethanol in step 3) is 1:1~2.

6. The process according to claim 1, in the first cooling interval in the cooling process of step 2), the temperature cools by a rate of 1.5-2.5° C./hour.

7. The process according to claim 1, centrifugation is performed when crystallization is completed, followed by washing and drying; wherein the methanol is used for washing, and air or vacuum is used for drying.

* * * * *